United States Patent [19]

Matsuyama et al.

[11] Patent Number: 5,371,014
[45] Date of Patent: Dec. 6, 1994

[54] PROCESS FOR THE PRODUCTION OF OPTICALLY ACTIVE 2-HYDROXY ACID ESTERS USING MICROBES TO REDUCE THE 2-OXO PRECURSOR

[75] Inventors: Akinobu Matsuyama; Teruyuki Nikaido; Yoshinori Kobayashi, all of Niigata, Japan

[73] Assignee: Daicel Chemical Industries, Ltd., Osaka, Japan

[21] Appl. No.: 139,878

[22] Filed: Oct. 22, 1993

Related U.S. Application Data

[63] Continuation of Ser. No. 819,679, Jan. 13, 1992, abandoned, which is a continuation of Ser. No. 415,325, Sep. 21, 1989, abandoned.

[30] Foreign Application Priority Data

| Feb. 12, 1988 | [JP] | Japan | 63-30476 |
| Feb. 12, 1988 | [JP] | Japan | 63-30477 |
| Apr. 28, 1988 | [JP] | Japan | 63-105892 |
| Apr. 30, 1988 | [JP] | Japan | 63-109938 |

[51] Int. Cl.$^5$ .......................... C12P 41/00; C12P 7/62
[52] U.S. Cl. ..................... 435/280; 435/135; 435/822; 435/911
[58] Field of Search ............... 435/135, 280, 136, 822, 435/911

[56] References Cited

U.S. PATENT DOCUMENTS

| 4,609,623 | 9/1986 | Leuchtenberger et al. | 435/130 |
| 4,785,089 | 11/1988 | Blaser et al. | 540/523 |
| 5,098,841 | 3/1992 | Ghisalba et al. | 435/280 |
| 5,256,552 | 10/1993 | Matsuyama et al. | 435/146 |

OTHER PUBLICATIONS

Deol et al., Aust. J. Chem., 29(11), pp. 2459-2467, 1976.
ATCC Catalogue of Fungi/Yeasts, 17th edition, pp. 324 and 346-347, 1987.

*Primary Examiner*—Douglas W. Robinson
*Assistant Examiner*—S. Saucier
*Attorney, Agent, or Firm*—Birch, Stewart, Kolasch & Birch

[57] ABSTRACT

An optically active 2-hydroxy acid derivative is produced by treating a 2-oxo acid derivative with a microorganism, which has been optionally treated, capable of asymmetrically reducing said 2-oxo acid derivative into an optically active (R)- or (S)-2-hydroxy acid derivative represented by the formula (II) and recovering the optically active (R)- or (S)-hydroxy acid derivative thus formed. Optically active 2-hydroxy acid derivatives are important intermediates in the synthesis of various drugs such as a remedy for hypertension.

28 Claims, No Drawings

PROCESS FOR THE PRODUCTION OF OPTICALLY ACTIVE 2-HYDROXY ACID ESTERS USING MICROBES TO REDUCE THE 2-OXO PRECURSOR

This application is a continuation, of application Ser. No. 07/819,679 filed on Jan. 13, 1992, now abandoned, which is a continuation application of Ser. No. 07/415,325, filed on Sep. 21, 1989, now abandoned.

TECHNICAL FIELD

This invention relates to a process for the production of an optically active 2-hydroxy acid derivative, for example, an ester. More Particularly, it relates to a process for the production of an optically active 2-hydroxy acid derivative which comprises treating a 2-oxo acid derivative represented by the formula (I) with a microorganism, which has been optionally treated, capable of asymmetrically reducing said 2-oxo acid derivative of the formula (I) into an optically active (R)- or (S)-2-hydroxy acid derivative represented by the formula (II) and recovering the optically active (R)- or (S)-2-hydroxy acid derivative of the formula (II) thus formed.

Optically active 2-hydroxy acid derivatives represented by the formula (II) are important intermediates in the synthesis of various drugs, for example, a remedy for hypertension.

BACKGROUND ART

Known methods for the production of optically active ethyl 2-hydroxy-4-phenylbutyrate, which is one of 2-hydroxy acid derivatives represented by the formula (II), include chemical and asymmetric reduction of (R)-2-hydroxy-4-phenylbutyric acid (cf. Eur. Pat. EP 206993) and chemical synthesis comprising synthesizing (R)-2-hydroxy-4-phenylbutyric acid from benzylmagnesium chloride and optically active glycidic acid followed by ethyl-esterification (cf. Japanese Patent Laid-Open No. 212329/1987).

However the former method comprising the asymmetric chemical reduction cannot give a satisfactory optical purity of the product, while the latter one comprising the chemical synthesis is disadvantageous in that optically active serine, which is the starting material for the optically active glycidic acid, is expensive for industrial uses.

Furthermore, no process for the production of an optically active 2-hydroxy acid derivative represented by the formula (II) from a 2-oxo acid derivative represented by the formula (I) by taking advantage of the capability of asymmetric reduction of a microorganism has been reported so far.

DISCLOSURE OF INVENTION

The present inventors have paid attention to a process for conveniently producing an optically active 2-hydroxy acid derivative represented by the formula (II) having a high optical purity through asymmetric reduction with a microorganism and attempted to find out microorganisms suitable for the above purpose. As a result, they have found that microorganisms belonging to the genera Lactobacillus, Leuconostoc, Streptococcus, Pediococcus, Guilliermondella, Candida, Saccharomycopsis, Zygosaccharomyces, Sporidiobolus, Rhodosporidium, Saccharomyces, Shizosaccharomyces, Pichia, Issatchinkia, Rhodotorula, Kluyveromyces, Filobasidium, Torulaspora, Sporobolomyces, Hansenula, Lipomyces, Lodderomyces, Pachysolen, Saccharomycodes, Achromobacter, Brevibacterium, Erwinia, Klebsiella, Psudomonas, Bacillus and Xanthomonas could asymmetrically reduce a 2-oxo acid derivative represented by the formula (I) to thereby give an optically active (R)-2-hydroxy acid derivative represented by the formula (II); and that microorganisms belonging to the genera Lactobacillus, Leuconostoc, Streptococcus, Sporolactobacillus, Ambrosiozima, Botryoascus, Bretanomyces, Clavispora, Candida, Saccharomyces, Zygosaccharomyces, Schizosaccharomyces, Saccharomycopsis, Sporobolomyces, Rhodotorula, Pichia, Hansenula, Syringospora, Stephanoascus, Trigonopsis, Wickerhamiella, Winge, Schwanniomyces, Geotrichum, Ashybya, Endomyces, Alcaligenes, Escherichia, Serratia, Pseudomonas, Pimelobacter, Bacillus, Brevibacterium, Staphylococcus, Aureobacterium, Flavobacterium, Paracoccus, Citrobacter, Protaminobacter, Rhodococcus, Micrococcus, Agrobacterium, Corynebacterium, Mycobacterium and Proteus could asymmetrically reduce a 2-oxo acid derivative represented by the formula (I) to thereby give an optically active (S)-2-hydroxy acid derivative represented by the formula (II), thus completing the present invention.

The 2-oxo acid derivative to be used as the starting material in the present invention is represented by the formula (I). Examples thereof include methyl, ethyl, propyl and butyl esters of benzoylformic, phenylpyruvic, 2-oxo-4-phenylbutyric and 2-oxo-5-phenylvaleric acids.

In the present invention, any microorganism belonging to the genus Lactobacillus, Leuconostoc, Streptococcus, Pediococcus, Guilliermondella, Candida, Saccharomycopsis, Zygosaccharomyces, Sporidiobolus, Rhodosporidium, Saccharomyces, Schizosaccharomyces, Pichia, Issatchinkia, Rhodotorula, Kluyveromyces, Filobasidium, Torulaspora, Sporobolomyces, Hansenula, Lipomyces, Lodderomyces, Pachysolen, Saccharomycodes, Achromobacter, Brevibacterium, Torulopsis, Chromobacterium, Erwinia, Klebsiella, Pseudomonas, Bacillus or Xanthomonas and capable of asymmetrically reducing a 2-oxo acid derivative represented by the formula (I) into an optically active (R)-2-hydroxy acid derivative represented by the formula (II) or one belonging to the genus Lactobacillus, Leuconostoc, Streptococcus, Sporolactobacillus, Ambrosiozyma, Botryoascus, Bretanomyces, Clavispora, Candida, Saccharomyces, Zygosaccharomyces, Shizosaccharomyces, Saccharomycopsis, Sporobolomyces, Rhodotorula, Pichia, Hansenula, Syringospora, Stephanoascus, Trigonopsis, Wickerhamiella, Winge, Schwanniomyces, Geotrichum, Ashybya, Endomyces, Alcaligenes, Escherichia, Serratia, Pseudomonas, Pimelobacter, Bacillus, Bacterium, Brevibacterium, Staphylococcus, Aureobacterium, Flavobacterium, Paracoccus, Citrobacter, Protaminobacter, Rhodococcus, Micrococcus, Agrobacterium, Corynebacterium, Mycobacterium or Proteus and capable of asymmetrically reducing a 2-oxo acid derivative represented by the formula (I) into an optically active (S)-2-hydroxy acid derivative represented by the formula (I) may be used.

Particular examples of the microorganism capable of producing an optically active (R)-2-hydroxy acid derivative represented by the formula (II) from a 2-oxo acid derivative represented by the formula (I) include *Lacto-* bacillus acidophilus NRIC1027 and IFO3831, Lactobacillus buchneri NRIC1027 and ATCC4005, Lactobacillus brevis IFO3960, Lactobacillus casei subsp. casei IFO12004, Lactobacillus cellobiosus NRIC1047 and ATCC11739, Lactobacillus collinoides NRIC1049 and ATCC27611, Lactobacillus coryniformis NRIC1051 and ATCC25600, Lactobacillus curvatus NRIC1052 and ATCC25601, Lactobacillus frigidus NRIC1079 and ATCC11307, Lactobacillus hilgardii NRIC1060 and ATCC 8290, Lactobacillus lactis NRIC1061 and ATCC123315, Lactobacillus malefermentas NRIC1081, Lactobacillus parvus NRIC1082 and ATCC11305, Lactobacillus sake NRIC1071 and ATCC15521, Lactobacillus salivarius NRIC1072 and ATCC11742, Lactobacillus vaccinistercus NRIC1075 and ATCC33310, Leuconostoc citrovorum NRIC1089, Leuconostoc cremoris NRIC1083 and ATCC19254, Leuconostoc dextranicum NRIC1085 and ATCC19255, Leuconostoc mesenteroides subsp. dextranicum IFO3349, Leuconostoc mesenteroides NRIC1088 and ATCC27307, Leuconostoc mesenteroides subsp. mesenteroides IFO3426, Streptococcus alactosus NRIC1154 and ATCC8058, Streptococcus equinus NRIC1139 and ATCC9812, Streptococcus faecium NRIC1145 and ATCC19434, Streptococcus uberis NRIC1153 and ATCC19436, Pediococcus parvulus IFO12233, Pediococcus pentosaceus IFO3891, Pediococcus sacidilactici ATCC8081, Gullliermondella selenospora IFO1850, Candida guilliermondii IAM4412, Saccharomycopsis fibuligera IFO0103, Saccharomycopsis capsularis IFO0672, Zygosaccharomyces bailii IFO1047, Sporidiobolus pararoseus AHU3447, Rhodosporidium diobovatum IFO0682, Rhodosporidium toruloides IFO0559, Saccharomyces rouxii IAM4011, Saccharomyces dairensis IFO0285, Torulaspora delbrueckii IFO0955, Schizosaccharomuyces pombe IFO0363, Pichia heedil IFO10019, Pichia membranaefaciens IFO0577, Pichia opuntiae var. thermotolerans IFO10024, Issatchinkia scutulata var scutulata IFO10069, Rhodotorula rubra AHU3243, Rhodotorula glutinis AHU3454, Kluyveromyces lactis IFO1267, Kluyveromyces drosphilarum IFO1012, Filobasidium capsuligenum IFO1185, Torulaspora delbrueckii IFO0381, Sporobolomyces rosenus IFO1037, Hansenula holsttii IFO0980, Hansenula subpelliculosa IFO0808, Sporidiobolus johnsonii IFO6903, Lipomyces starkeyi IFO1289, Lodderomyces elongisporus IFO1676, Pachysolen tannophilus IFO1007, Saccharomycodes ludwigii IFO0798, Achromobacter pestifer ATCC23584, Brevibacterium iodinum IFO3558, Erwinia carotovora IFO3880, Klebsiella pneumoniae IAM1063, Pseudomonas dacunhae IFO12048, Bacillus licheniformis IFO12200, Bacillus cereus IFO3001 and Xanthomonas oryzae IAM1657.

Examples of the microorganism capable of producing an optically active (S)-2-hydroxy acid derivative represented by the formula (II) from a 2-oxo acid derivative represented by the formula (I) include Lactobacillus brevis NRIC1037 and ATCC4006, Lactobacillus bulgaricus NRIC1041 and IAM1120, Lactobacillus casei NRIC1044 and ATCC25598, Lactobacillus casei subsp. rhamnosus IFO3425, Lactobacillus fructosus NRIC1058 and ATCC12315, Lactobacillus delbrueckii AHU1056, Lactobacillus leichmannii AHU1681, Lactobacillus paintatum IFO3070, Lactobacillus viridescens NRIC1073 and ATCC12706, Lactobaciilus xylosus NRIC1074 and ATCC15577, Lactobacillus yamanashiensis NRIC1076 and ATCC27304, Leuconosotc mesenteroides AHU1067, Leuconostoc dextranicum AHU1080, Streptococcus agalactiae NRIC1137 and ATCC13813, Streptococcus lactis NRIC1149 and ATCC19435, Streptococcus faecalis IFO12964, Sporolactobacillus inulinus NRIC1133 and ATCC15538, Ambrosiozyma cicatricosa IFO1846, Botryoascus synnaedendrus IFO1604, Bretanomyces bruxellensis IFO0268, Clavispora lusitaniae IFO1019, Candida humicola IFO0760, Candida parasilosis IFO1396, Candida pseudotropicalis IAM4829, Candida utilis IAM4220, Candida rugosa IFO0750, Saccharomyces bayanus IFO0262, Saccharomyces cerevisiae ATCC9080, Saccharomyces kluyveri IFO1893, Saccharomyces uvarum IFO0565, Saccharomyces chevalieri IFO0222, Zygosaccharomyces fermentati IFO0021, Shizosaccharomyces octosporus IFO0353, Saccharomycopsis lipolytica IFO1551, Sporobolomyces salmonicolor AHU3982, Rhodotolura glutinis IFO0389, Rhodotorula minuta IFO0387, Pichia opuntiae var. thermotolerans IFO10025, Pichia burtonii IFO1986, Pichia farinosa IFO1163, Hansenula fabianii IFO1254, Syringospora albicans IFO1856, Stephanoascus ciferrii IFO1854, Trigonopsis variabilis IFO0755, Wickerhamiella domercqii IFO1857, Wingea robertsii IFO1277, Schwanniomyces occidentalis IFO1841, Geotrichum candidum IFO4601, Ashbya gossypii IFO1355, Endomyces decipiens IFO0102, Alcaligenes faecalis IAM1015, Esherichia coli IFO3544, Serratia marcescens IFO3046, Pseudomonas aureofaciens IFO3522, Pseudomonas fluorescens IFO3925, Pseudomonas riboflavina IFO13584, Pseudomonas chlororaphis IFO3904, Pimelobacter simplex IFO12069, Bacillus subtilis IFO3007, Brevibacterium ammoniagenes IAM1641, Staphylococcus aureus IFO3060, Aureobacterium testaceu IFO12675, Flavobacterium suaveolens IFO3752, Paracoccus denitrificans IFO12442, Citrobacter freundii AHU1534, Protaminobacter ruber IAM1081, Rhodococcus equil IFO3730, Micrococcus luteus IFO12992, Agrobacterium radiobacter IFO12664, Corynebacterium glutamicum ATCC13032, Mycobacterium smegmatis IFO3153 and Proteus vulgaris IFO3851.

Each strain may be either a wild type, a variant or a recombinant obtained by genetic engineering such as cell fusion or gene recombination.

Microorganisms having IFO numbers assigned thereto are described in the List of Culture, 8th ed., vol. 1 (1988) published by the Institute for Fermentation, Osaka (IFO) and available therefrom. Those having AHU numbers are described in the Catalogue Culture, 4th ed. (1987) published by Japan Federation of Culture Collection (JFCC) and available from the Faculty of Agriculture, Hokkaido University. Those having ATCC numbers are described in the Catalogue of Bacteria phages rDNA Vectors, 16th ed. (1985) published by American Type Culture Collection (ATCC) and available therefrom. Those having NRIC numbers are described in the Culture Collection of NODAI No. 1 (1985) published by Tokyo University of Agriculture and available therefrom. Those having IAM numbers are available from the Institute of Applied Microbiology, the University of Tokyo.

The microorganism to be used in the present invention may be cultured in any medium so long as it can grow therein. Any carbon source may be used so long as said microorganism can utilize it. Examples thereof include sugars such as glucose, fructose, sucrose and dextrin, alcohols such as sorbitol, ethanol and glycerol, organic acids such as fumaric, citric, acetic and propionic acids and salts thereof, hydrocarbons such as paraffin and mixtures thereof. Examples of a nitrogen source include ammonium salts of inorganic acids, such as ammonium chloride, ammonium sulfate and ammonium phosphate, ammonium salts of organic acids, such as ammonium fumarate and ammoniumcitrate, nitrogenous materials such as meat extract, yeast extract, corn steep liquor, casein hydrolysate and urea and mixtures thereof. Furthermore various nutritional sources commonly used in the culture of microorganisms, such as inorganic salts, trace metal salts and vitamins, may be appropriately mixed and used in the present invention. In addition, materials effective in promoting the growth of the microorganism, in elevating the productivity of the target compound or in maintaining the pH value of the medium on the desired level may be added, if required.

The pH value of the medium may be adjusted to 3.0 to 9.5, preferably 5 to 8. The culture may be carried out at a temperature of 20° to 45° C., preferably 25° to 37° C., either aerobically or anaerobically under conditions suitable for the growth of the microorganism for 15 to 120 hours, preferably 12 to 72 hours.

The reduction may be effected by using the culture medium as such. Alternately, the cells may be separated by, for example, centrifugation, optionally washed and resuspended in a buffer solution or water. Then a 2-oxo acid derivative represented by the formula (I) may be added to the suspension thus obtained. In this reaction, it is sometimes preferable to add a carbon source such as glucose or sucrose to the medium to thereby supply energy. The cells may be used as such in the form of viable cells. Alternately, they may be ground, treated with acetone or lyophilized. These cells, which have been optionally treated, may be immobilized prior to the use by a conventional method such as the polyacrylamide gel, carrageenan gel, alginic acid gel or agar gel method. Furthermore, an enzyme obtained from said treated cells by combining known methods may be used in the present invention.

The 2-oxo acid derivative represented by the formula (I) may be added either at once at the initiation of the reaction or by portions either as such, dissolved in water or an inert organic solvent or dispersed in, for example, a surfactant.

The reaction may be conducted at a pH value of 3 to 9, preferably 5 to 8, at 10° to 60° C., preferably 20° to 40° C. for 1 to 120 hours with or without stirring. The concentration of the substrate may preferably range from 0.1 to 10%, though it is not restricted thereby.

The optically active (R)- or (S)-2-hydroxy acid derivative represented by the formula (II) thus produced may be readily collected by extracting the reaction mixture, from which the cells may be optionally separated, with an organic solvent and purifying the extract by, for example, column chromatography or recrystallization.

BEST MODE FOR CARRYING OUT THE INVENTION

To further illustrate the present invention, and not by way of limitation, the following Examples will be given.

In each Example, the absolute configuration and optical purity were determined by extracting the reaction product with ethyl acetate and subjecting the obtained extract to high performance liquid chromatography by using an optical resolution column Column: Chiral cell OB, mfd. by Daicel Chemical Industries, Ltd., 4.6 mm (i.d.)×250 mm, solvent: n-hexane : 2-propanpol (19 : 1 v/v), flow rate: 0.5 ml/min, Detection: 254 nm]. The reaction yield was determined by gas chromatography [column: PEG20M, 10%, 2 m, 200° C.].

EXAMPLE 1

100 ml of a medium comprising 2% of glucose, 0.5% of yeast extract, 0.3% of peptone, 0.3% of meat extract, 0.1% of monopotassium phospate, 0.2% of dipotassium phosphate and 0.5% of calcium carbonate was introduced into a 500-ml Erlenmeyer flask and sterilized. Next, each strain specified in Table 1 was inoculated thereto and cultured therein at 30° C. for 30 hours under rotation and shaking.

After the completion of the culture, the cells were separated by centrifugation and washed once with a physiological saline solution to thereby give viable cells.

7.5 ml of distilled water was introduced into a 100-ml Erlenmeyer flask and the above viable cells were suspended therein. 1.2 g of glucose was added to the suspension thus obtained and the resulting mixture was shaken under rotation at 30° C. for 10 minutes. Then 0.1 g of ethyl 2-oxo-4-phenylbutyrate and 0.3 g of calcium carbonate were added thereto and the resulting mixture was shaken under rotation at 30° C. for 20 hours.

After the completion of the reaction, the optically active ethyl 2-hydroxy-4-phenylbutyrate thus formed was extracted with 20 ml of ethyl acerate.

The ethyl acetate phase was analyzed by gas chromatography and the reaction yield was determined. Next, a given amount of the ethyl acetate phase was dehydrated with anhydrous Glauber's salt and the solvent was removed therefrom. The oily product thus obtained was dissolved in ethanol and subjected to high performance liquid chromatography. The absolute configuration and optical purity of the optically active ethyl 2-hydroxy-4-phenylbutyrate thus obtained were determined.

Table 1 shows the results.

EXAMPLE 2

100 ml of a YM medium comprising 0.3% of yeast extract, 0.3% of malt extract, 0.5% of peptone and 2% of glucose (pH 6.0) was introduced into a 500-ml Sakaguchi flask and sterilized. Then each strain specified in Table 2 was inoculated thereto and cultured therein at 30° C. for 48 hours under shaking.

After the completion of the culture, the cells were separated by centrifugation and washed once with a physiological saline solution to thereby give viable cells.

50 ml of distilled water was introduced into a 500-ml Sakaguchi flask and the abovementioned viable cells were suspended therein. Then 6 g of sucrose was added to the obtained suspension and the mixture was reciprocally shaken at 30° C. for 10 minutes. Next, 0.5 g of ethyl 2-oxo-4-phenylbutyrate was added thereto and the resulting mixture was reciprocally shaken at 30° C. for 20 hours.

After the completion of the reaction, the reaction yield, absolute configuration and optical purity of the optically active ethyl 2-hydroxy-4-phenylbutyrate thus obtained were determined in the same manner as the one described in Example 1.

Table 2 shows the results.

EXAMPLE 3

Each microorganism specified in Table 3 was subjected to the same treatment as that described in Example 1 except that the medium contained no calcium carbonate and had a pH value of 7 and that the culture was reciprocally conducted in a 500-ml Sakaguchi flask.

After the completion of the reaction, the reaction yield, absolute configuration and optical purity of the optically active ethyl 2-hydroxy-4-phenylbutyrate thus obtained were determined in the same manner as the one described in Example 1.

Table 3 shows the results.

EXAMPLE 4

Leuconostoc mesenteroides subsp. dextranicum IFO3349 was inoculated into 2-l of the same medium as the one described in Example 2 in a 5-l jar fermenter and cultured therein at 30° C. under stirring at 100 rpm for 30 hours.

After the completion of the culture, the cells were collected by centrifugation and washed with 1-l of water. Then these cells were suspended in 200 ml of water and introduced into a 1-l Erlenmeyer flask. Next, 2 g of ethyl 2-oxo-4-phenylbutyrate, 20 g of glucose and 2 g of calcium carbonate were added thereto and the obtained mixture was allowed to react at 30° C. under stirring for 48 hours.

After the completion of the reaction, the reaction mixture was extracted with 100-ml portions of ethyl acetate twice. The ethyl acetate phase was dehydrated with anhydrous Glauber's salt and the solvent was removed therefrom under reduced pressure. Then it was distilled in a conventional manner under reduced pressure of 0.5 mmHg (b.p.: 115°–118° C.). Thus 1.4 g of the aimed ethyl (R)-2-hydroxy-4-phenylbutyrate was obtained (yield: 70%, optical purity: 82% e.e.).

EXAMPLE 5

Pseudomonas aureofaciens IFO3522 was inoculated into 2-l of the same medium as the one described in Example 1 except containing no calcium carbonate in a 5-l jar fermenter and cultured therein at 30° C. under stirring at 4.00 rpm and aerating at 1 vvm for 30 hours.

After the completion of the culture, the cells were collected by centrifugation and washed with 1-l of water. Then these cells were suspended in 200 ml of water and introduced into a 1-l Erlenmeyer flask. Twenty g of ethyl 2-oxo-4-phenylbutyrate, 20 g of glucose and 2 g of calcium carbonate were added thereto and the obtained mixture was allowed to react at 30° C. under stirring for 48 hours.

After the completion of the reaction, the reaction mixture was extracted with 100-ml portions of ethyl acetate twice. The ethyl acetate phase was dehydrated with anhydrous Glauber's salt and the solvent was removed therefrom under reduced pressure. Then it was distilled in a conventional manner under reduced pressure of 0.5 mmHg (b.p.: 115°–118° C.). Thus 0.7 g of the aimed ethyl (S)-2-hydroxy-4-phenylbutyrate was obtained (yield: 35%, optical purity: 96% e.e.).

The process of the present invention for the production of an optically active 2-hydroxy acid derivative through asymmetric reduction by using a microorganism makes it possible to readily produce an optically active 2-hydroxy acid derivative having a high optical purity. Thus it is highly advantageous as an industrial process.

TABLE 1

| Microorganism | Yield (%) | Optically active ethyl 2-hydroxy-4-phenylbutyrate | |
|---|---|---|---|
| | | Absolute configuration | Optical purity (% e.e.) |
| Lactobacillus acidophilus NRIC1027 | 10 | R | 61 |
| Lactobacillus buchneri NRIC1040 | 12 | R | 54 |
| Lactobacillus brevis IFO3960 | 8 | R | 100 |
| Lactobacillus casei subsp. casei IFO12004 | 16 | R | 100 |
| Lactobacillus cellobiosus NRIC1047 | 11 | R | 53 |
| Lactobacillus collinoides NRIC1049 | 12 | R | 60 |
| Lactobacillus coryniformis NRIC1051 | 13 | R | 33 |
| Lactobacillus curvatus NRIC1052 | 13 | R | 56 |
| Lactobacillus frigidus NRIC1079 | 12 | R | 57 |
| Lactobacillus hilgardii NRIC1060 | 13 | R | 39 |
| Lactobacillus lactis NRIC1061 | 96 | R | 49 |
| Lactobacillus malefermentans NRIC1081 | 13 | R | 61 |
| Lactobacillus parvus NRIC1082 | 73 | R | 22 |
| Lactobacillus sake NRIC1071 | 14 | R | 24 |
| Lactobacillus salivarius NRIC1072 | 13 | R | 58 |
| Lactobacillus vaccinistercus NRIC1075 | 13 | R | 45 |
| Leuconostoc citrovorum NRIC1089 | 77 | R | 35 |
| Leuconostoc cremoris NRIC1083 | 12 | R | 57 |
| Leuconostoc dextranicum NRIC1085 | 17 | R | 24 |
| Leuconostoc mesenteroides subsp. dextranicum IFO3349 | 45 | R | 74 |
| Leuconostoc mesenteroides NRIC1088 | 21 | R | 25 |
| Leuconostoc mesenteroides subsp. mesenteroides IFO3426 | 27 | R | 20 |
| Streptococcus alactosus NRIC1154 | 10 | R | 25 |
| Streptococcus equinus NRIC1139 | 12 | R | 91 |
| Streptococcus faecium | 93 | R | 53 |
| Streptococcus uberis NRIC1153 | 80 | R | 40 |
| Pediococcus parvulus IFO12233 | 18 | R | 20 |
| Pediococcus pentosaceus IFO3891 | 39 | R | 22 |
| Pediococcus acidilactici ATCC8081 | 56 | R | 37 |
| Lactobacillus brevis NRIC1037 | 59 | S | 65 |
| Lactobacillus bulgaricus NRIC1041 | 13 | S | 20 |
| Lactobacillus casei NRIC1044 | 36 | S | 20 |
| Lactobacillus casei subsp. rhamnosus IFO3425 | 35 | S | 20 |
| Lactobacillus fructosus NRIC1058 | 12 | S | 50 |
| Lactobacillus delbrueckii AHU1056 | 37 | S | 20 |
| Lactobacillus leichmannii AHU1681 | 44 | S | 40 |

TABLE 1-continued

| Microorganism | Yield (%) | Optically active ethyl 2-hydroxy-4-phenylbutyrate | |
|---|---|---|---|
| | | Absolute configuration | Optical purity (% e.e.) |
| Lactobacillus plantarum IFO3070 | 30 | S | 96 |
| Lactobacillus viridescens NRIC1073 | 55 | S | 72 |
| Lactobacillus xylosus NRIC1074 | 59 | S | 20 |
| Lactobacillus yamanashiensis NRIC1076 | 13 | S | 33 |
| Leuconostoc mesenteroides AHU1067 | 15 | S | 84 |
| Leuconostoc dextranicum AHU1080 | 19 | S | 20 |
| Streptococcus agalactiae NRIC1137 | 95 | S | 68 |
| Streptococcus lactis NRIC1149 | 26 | S | 76 |
| Streptococcus faecalis IFO12964 | 33 | S | 85 |
| Sporolactobacillus inulinus NRIC1133 | 10 | S | 91 |

TABLE 2

| Microorganism | Yield (%) | Optically active ethyl 2-hydroxy-4-phenylbutyrate | |
|---|---|---|---|
| | | Absolute configuration | Optical purity (% e.e.) |
| Guilliermondella selenospora IFO1850 | 10 | R | 20 |
| Candida guilliermondii IAM4412 | 16 | R | 40 |
| Saccharomycopsis fibuligera IFO0103 | 10 | R | 22 |
| Saccharomycopsis capsularis IFO0672 | 10 | R | 20 |
| Zygosaccharomyces bailii IFO1047 | 23 | R | 20 |
| Sporidiobolus pararoseus AHU3447 | 25 | R | 99 |
| Rhodosporidium diobovatum IFO0682 | 42 | R | 72 |
| Rhodosporidium toruloides IFO0559 | 10 | R | 100 |
| Saccharomyces rouxii IAM4011 | 14 | R | 78 |
| Saccharomyces dairensis IFO0285 | 29 | R | 42 |
| Torulaspora delbrueckii IFO0955 | 58 | R | 20 |
| Schizosaccharomyces pombe IFO0363 | 34 | R | 20 |
| Pichia heedii IFO10019 | 21 | R | 69 |
| Pichia membranaefaciens IFO0577 | 47 | R | 33 |
| Pichia opuntiae var. thermotolerans IFO10024 | 35 | R | 20 |
| Issatchinkia scutulata var. scutulata IFO10069 | 26 | R | 56 |
| Rhodotorula rubra AHU3243 | 23 | R | 57 |
| Rhodotorula glutinis AHU3454 | 41 | R | 48 |
| Kluyveromyces lactis IFO1267 | 43 | R | 32 |
| Kluyveromyces drosophilarum IFO1012 | 45 | R | 20 |
| Filobasidium capsuligenum IFO1185 | 8 | R | 46 |
| Torulaspora delbrueckii IFO0381 | 70 | R | 45 |
| Sporobolomyces roseus IFO1037 | 11 | R | 62 |
| Hansenula holsttii IFO0980 | 27 | R | 32 |
| Hansenula subpelliculosa IFO0808 | 32 | R | 34 |
| Sporidiobolus johnsonii IFO6903 | 51 | R | 22 |
| Lipomyces starkeyi IFO1289 | 10 | R | 24 |
| Lodderomyces elongisporus IFO1676 | 52 | R | 26 |
| Pachysolen tannophilus IFO1007 | 26 | R | 20 |
| Saccharomycodes ludwigii IFO0798 | 10 | R | 21 |
| Ambrosiozyma cicatricosa IFO1846 | 11 | S | 46 |
| Botryoascus synnaedendrus IFO1604 | 16 | S | 19 |
| Bretanomyces bruxellensis IFO0628 | 19 | S | 20 |
| Clavispora lusitaniae IFO1019 | 31 | S | 30 |
| Candida humicola IFO0760 | 10 | S | 26 |
| Candida parapsilosis IFO1396 | 50 | S | 20 |
| Candida pseudotropicalis IAM4829 | 10 | S | 62 |
| Candida utilis IAM4220 | 35 | S | 53 |
| Candida rugosa IFO0750 | 21 | S | 71 |
| Saccharomyces bayanus IFO0262 | 96 | S | 43 |
| Saccharomyces cerevisiae ATCC9080 | 15 | S | 32 |
| Saccharomyces kluyveri IFO1893 | 35 | S | 65 |
| Saccharomyces uvarum IFO0565 | 20 | S | 33 |
| Saccharomyces chevalieri IFO0222 | 96 | S | 40 |
| Zygosaccharomyces fermentati IFO0021 | 32 | S | 20 |
| Schizosaccharomyces octosporus IFO0353 | 26 | S | 40 |
| Saccharomycopsis lipolytica IFO1551 | 10 | S | 61 |
| Sporobolomyces salmonicolor AHU3982 | 45 | S | 20 |
| Rhodotorula glutinis IFO0389 | 10 | S | 37 |
| Rhodotolura minuta IFO0387 | 10 | S | 20 |
| Pichia opuntiae var. thermotolerans IFO10025 | 10 | S | 34 |
| Pichia burtonii IFO1986 | 12 | S | 71 |
| Pichia farinosa IFO1163 | 20 | S | 67 |
| Hansenula fabianii IFO1254 | 43 | S | 36 |
| Syringospora albicans IFO1856 | 58 | S | 32 |
| Stephanoascus ciferrii IFO1854 | 12 | S | 48 |
| Trigonopsis variabilis IFO0755 | 25 | S | 69 |
| Wickerhamiella domercqii IFO1857 | 63 | S | 41 |
| Wingea robertsii | 19 | S | 42 |

TABLE 2-continued

| Microorganism | Yield (%) | Optically active ethyl 2-hydroxy-4-phenylbutyrate Absolute configuration | Optical purity (% e.e.) |
|---|---|---|---|
| IFO1277 | | | |
| *Schwanniomyces occidentalis* IFO1841 | 17 | S | 31 |
| *Geotrichum candidum* IFO4601 | 34 | S | 28 |
| *Ashbya gossypii* IFO1355 | 37 | S | 100 |
| *Endomyces decipiens* IFO0102 | 32 | S | 100 |

TABLE 3

| Microorganism | Yield (%) | Optically active ethyl 2-hydroxy-4-phenylbutyrate Absolute configuration | Optical purity (% e.e.) |
|---|---|---|---|
| *Achromobacter pestifer* ATCC23584 | 14 | R | 100 |
| *Brevibacterium iodinum* IFO3558 | 30 | R | 62 |
| *Erwinia carotovora* IFO3830 | 11 | R | 100 |
| *Klebsiella pneumoniae* IAM1063 | 12 | R | 100 |
| *Pseudomonas dacunhae* IFO12048 | 13 | R | 100 |
| *Bacillus licheniformis* IFO12200 | 11 | R | 100 |
| *Bacillus cereus* IFO3001 | 12 | R | 21 |
| *Xanthomonas oryzae* IAM1657 | 37 | R | 20 |
| *Alcaligenes faecalis* IAM1015 | 24 | S | 97 |
| *Escherichia coli* IFO3544 | 34 | S | 94 |
| *Serratia marcescens* IFO3046 | 40 | S | 89 |
| *Pseudomonas aureofaciens* IFO3522 | 36 | S | 95 |
| *Pseudomonas fluorescens* IFO3925 | 49 | S | 54 |
| *Pseudomonas riboflavina* IFO13584 | 12 | S | 56 |
| *Pseudomonas chlororaphis* IFO3904 | 46 | S | 76 |
| *Pimelobacter simplex* IFO12069 | 11 | S | 100 |
| *Bacillus subtilis* IFO3007 | 15 | S | 71 |
| *Brevibacterium ammoniagenes* IAM1641 | 18 | S | 80 |
| *Staphylococcus aureus* IFO3060 | 23 | S | 85 |
| *Aureobacterium testaceum* IFO12675 | 41 | S | 62 |
| *Flavobacterium suaveolens* IFO3752 | 23 | S | 85 |
| *Paracoccus denitrificans* IFO12442 | 11 | S | 74 |
| *Citrobacter freundii* AHU1534 | 18 | S | 56 |
| *Protaminobacter ruber* IAM1081 | 21 | S | 43 |
| *Rhodococcus equii* IFO3730 | 11 | S | 100 |
| *Micrococcus luteus* IFO12992 | 10 | S | 24 |
| *Agrobacterium radiobacter* IFO12664 | 16 | S | 35 |
| *Corynebacterium glutamicum* ATCC13032 | 54 | S | 20 |

TABLE 3-continued

| Microorganism | Yield (%) | Optically active ethyl 2-hydroxy-4-phenylbutyrate Absolute configuration | Optical purity (% e.e.) |
|---|---|---|---|
| *Mycobacterium smegmatis* IFO3153 | 15 | S | 21 |
| *Proteus vulgaris* IFO3851 | 12 | S | 30 |

We claim:

1. A process for the production of an optically active 2-hydroxy acid derivative represented by the formula (II):

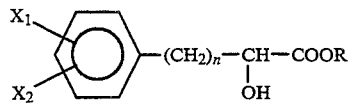

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

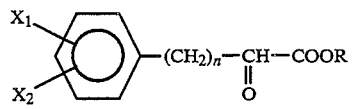

wherein $X_1$, $X_2$, R and n are as previously defined, with a microorganism capable of asymmetrically reducing said 2-oxo acid derivative of the formula (I) into an optically active (R)-form of said 2-hydroxy acid derivative of the formula (II), wherein said microorganism is selected from the group consisting of:
Sporidiobolus pararoseus;
Rhodosporidium toruloides;
Lactobacillus casei;
Leuconostoc mesenteroides subsp. dextranicum; and
Streptococcus equinus;
and recovering the optically active (R)-2-hydroxy acid derivative of the formula (II) so produced.

2. A process for the production of an optically active 2-hydroxy acid derivative represented by the formula (II):

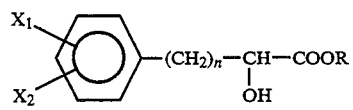

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

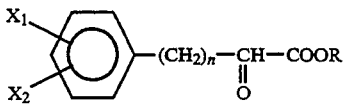

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism is selected from the group consisting of:

Lactobacillus plantarum;
Ashbya gossypii;
Serratia marcescens;
Esherichia coli;
Pseudomonas aureofaciens;
Leuconostoc mesenteroides;
Streptococcus faecalis;
Sporolactobacillus inulinus;
Candida rugosa;
Pichia burtonii;
Trigonopsis variabilis;
Flavobacterium suaveolens; and
Paracoccus denitrificans;

and recovering the optically active (S)-2-hydroxy acid derivative of the formula (II) so produced.

3. A process for the production of an optically active 2-hydroxy acid derivative represented by the formula (II):

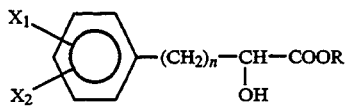

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

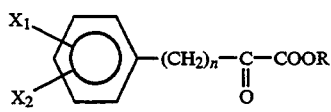

wherein [$X_1$ and $X_2$ represent each a hydrogen atom, a halogen atom, a hydroxyl group, a nitro group or an alkyl group, R represents an alkyl or a phenyl group, and n is an integer ranging from 0 to 3,]$X_1$, $X_2$, R and n are as previously defined, with a microorganism capable of asymmetrically reducing said 2-oxo acid derivative of the formula (I) into an optically active (R) form of said 2-hydroxy acid derivative of the formula (II), wherein said microorganism is selected from the group consisting of:

| | | |
|---|---|---|
| Lactobacillus casei | [IF012004] | IFO 12004 |
| Leuconostoc mesenteroides subsp. dextranicum | [IF03349] | IFO 3349 |
| Rhodosporidium toruloides | [IF00559] | IFO 0559 |
| [Saccharomyces rouxii | IAM4011] | | and recovering the optically active (R)-2-hydroxy acid derivative of the formula (II) so produced.

4. A process as in claim 3, wherein said 2-oxo acid derivative to be used as the starting material is selected from the group consisting of methyl, ethyl, propyl, and butyl esters of benzoylformic, phenylpyruvic, 2-oxo-4-phenylbutyric and 2-oxo-5-phenylvaleric acids.

5. A process as in claim 3, wherein said 2-oxo acid derivative used as the starting material is the ethyl ester of 2-oxo-4-phenylbutyric acid.

6. The process of claim 3, wherein said microorganism has been collected from the culture and resuspended in an aqueous medium prior to treating the said 2-oxo acid.

7. The process of claim 3, wherein said microorganism has been collected from the culture and the cells are ground, treated with acetone, or lyophilized prior to treating the said 2-oxo acid.

8. A process for the production of an optically active 2-hydroxy acid derivative represented by the formula (II):

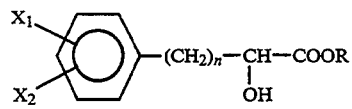

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula ( I ):

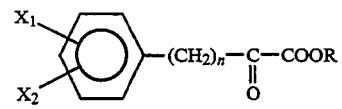

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism is selected from the group consisting of:

| | | |
|---|---|---|
| Lactobacillus plantarum | [IF03070] | IFO 3070 |
| Leuconostoc mesenteroides | [AHU1067] | AHU 1067 |
| Streptococcus faecalis | [IF012964] | IFO 12964 |
| Sporolactobacillus inulinus | [NRIC1133] | NRIC 1133 |
| [Candida pseudotropicalis | IAM4829] | |
| Candida rugosa | [IF00750] | IFO 0750 |
| Pichia burtonii | [IF01986] | IFO 1986 |
| Trigonopsis variabilis | [IF00755] | IFO 0755 |
| Ashbya gossypii | [IF01355] | IFO 1355 |
| [Endomyces decipiens | IF00102] | |
| Esherichia coli | [IF03544] | IFO 3544 |
| Serratia marcescens | [IF03046] | IFO 3046 |
| Pseudomonas aureofaciens | [IF03522] | IFO 3522 and |
| [Brevibacterium ammoniagenes | JAM1641] | | and recovering the optically active (S)-2-hydroxy acid derivative of the formula (II) so produced.

9. A process as in claim 8, wherein said 2-oxo acid derivative to be used as the starting material is selected from the group consisting of methyl, ethyl, propyl, and butyl esters of benzoylformic, phenylpyruvic, 2-oxo-4-phenylbutyric and 2-oxo-5-phenylvaleric acids.

10. A process as in claim 8, wherein said 2-oxo acid derivative used as the starting material is the ethyl ester of 2-oxo-4-phenyl butyric acid.

11. The process of claim 8, wherein said microorganism has been collected from the culture and resuspended in an aqueous medium prior to treating the said 2-oxo acid.

12. The process of claim 8, wherein said microorganism has been collected from the culture and the cells ground, treated with acetone, or lyophilized prior to treating the said 2-oxo acid.

13. A process for the production of an optically active 2-hydroxy acid derivative represented by the formula (II):

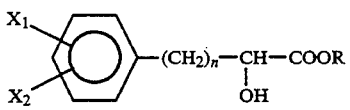

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

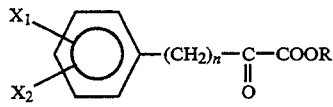

wherein $X_1$, $X_2$, R and n are as previously defined, with a microorganism capable of asymmetrically reducing said 2-oxo acid derivative of the formula (I) into an optically active (R)- form of said 2-hydroxy acid derivative of the formula (II), wherein said microorganism is selected from the group consisting of:

| | | |
|---|---|---|
| Streptococcus equinus | [NRIC1139] | NRIC 1139 |
| Sporidiobolus pararoseus | [AHU3447] | AHU 3447 |
| Rhodosporidium toruloides | [IFO0559] | IFO 0559 and |
| [Saccharomyces rouxii | IAM4011] | | and recovering the optically active (R)-2-hydroxy acid derivative of the formula (II) so produced.

14. A process for the production of an optically active 2-hydroxy acid derivative represented by the formula (II):

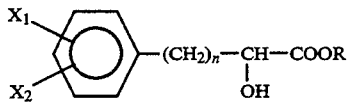

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

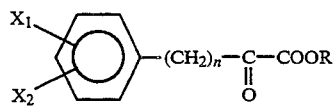

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism is selected from the group consisting of:

| | | |
|---|---|---|
| Streptococcus faecalis | [IF012964] | IFO 12964 |
| Sporolactobacillus inulinus | [NRIC1133] | NRIC 1133 |
| [Candida pseudotropicalis | IAM4829] | |
| Candida rugosa | [IF00750] | IFO 0750 |
| Pichia burtonii | [IF01986] | IFO 1986 |
| Trigonopsis variabilis | [IF00755] | IFO 0755 |
| Ashbya gossypii | [IF01355] | IFO 1355 |
| [Endomyces decipiens | IF00102] | |
| Esherichia coli | [IF03544] | IFO 3544 |
| Serratia marcescens | [IF03046] | IFO 3046 |
| Pseudomonas aureofaciens | [IF03522] | IFO 3522 |
| [Pseudomonas fluorescens | IF03925] | |
| [Brevibacterium ammoniagenes | IAM1641] | |
| Flavobacterium suaveolens | [IF03752] | IFO 3752 and |
| Paracoccus denitrificans | [IF012442] | IFO 12442 | and recovering the optically active (S)-2-hydroxy acid derivative of the formula (II) so produced.

15. A process for the production of an optically active 2-hydroxy acid derivative represented by the formula (II):

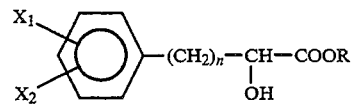

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

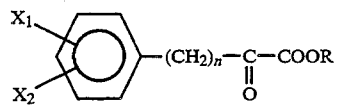

wherein $X_1$, $X_2$, R and n are as previously defined, with a microorganism capable of asymmetrically reducing said 2-oxo acid derivative of the formula (I) into an optically active (R)-form of said 2-hydroxy acid derivative of the formula (II), wherein said microorganism is selected from the group consisting of:

| | | |
|---|---|---|
| Lactobacillus casei subsp. casei | [IF012004] | IFO 12004 |
| Leuconostoc mesenteroides subsp. dextranicum | [IF03349] | IFO 3349 |
| Streptococcus equinus | [NRIC1139] | NRIC 1139 |
| Sporidiobolus pararoseus | [AHU3447] | AHU 3447 |
| Rhodosporidium toruloides | [IF00559] | IFO 0559 and |

-continued

| | | |
|---|---|---|
| [*Saccharomyces rouxii* | IAM4011] | | and recovering the optically active (R)-2-hydroxy acid derivative of the formula (II) so produced.

16. The process of claim 15, wherein said microorganism has been collected from the culture and resuspended in an aqueous medium prior to treating the said 2-oxo acid.

17. The process of claim 15, wherein said microorganism has been collected from the culture and the cells ground, treated with acetone, or lyophilized prior to treating the said 2-oxo acid.

18. A process for the production of an optically active 2-hydroxy acid derivative represented by the formula (II):

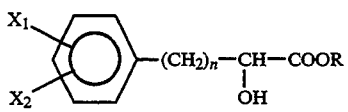

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

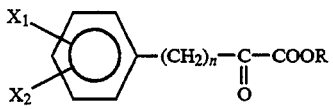

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism is selected from the group consisting of:

| | | |
|---|---|---|
| *Lactobacillus plantarum* | [IF03070] | IFO 3070 |
| *Streptococcus faecalis* | [IF012964] | IFO 12964 |
| *Sporolactobacillus inulinus* | [NRIC1133] | NRIC 1133 |
| *Candida rugosa* | [IF00750] | IFO 0750 |
| *Pichia burtonii* | [IF01986] | IFO 1986 |
| *Ashbya gossypii* | [IF01355] | IFO 1355 |
| [*Endomyces decipiens* | IF00102] | |
| *Esherichia coli* | [IF03544] | IFO 3544 |
| *Serratia marcescens* | [IF03046] | IFO 3046 |
| *Pseudomonas aureofaciens* | [IF03522] | IFO 3522 |
| [*Bacillus subtilis* | IF03007] | |
| [*Brevibacterium ammoniagenes* | IAM1641] | |
| *Flavobacterium suaveolens* | [IF03752] | IFO 3572 and |
| *Paracoccus denitrificans* | [IF012442] | IFO 12442 | and recovering the optically active (S)-2-hydroxy acid derivative of the formula (II) so produced.

19. The process of claim 16, wherein said microorganism has been collected from the culture and resuspended in an aqueous medium prior to treating the said 2-oxo acid.

20. The process of claim 18, wherein said microorganism has been collected from the culture and the cells ground, treated with acetone, or lyophilized prior to treating the said 2-oxo acid.

21. A process for the production of an optically active 2-hydroxy acid derivative represented by the formula (II):

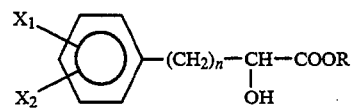

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

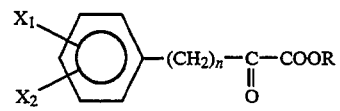

wherein $X_1$, $X_2$, R and n are as previously defined, with a microorganism capable of asymmetrically reducing said 2-oxo acid derivative of the formula (I) into an optically active (R)-form of said 2-hydroxy acid derivative of the formula (II), wherein said microorganism is selected from the group consisting of:

| | | |
|---|---|---|
| *Sporidiobolus pararoseus* | [AHU3447] | AHU 3447 |
| *Rhodosporidium toruloides* | [IF00559] | IFO 0559 |
| [*Saccharomyces rouxii* | IAM4011] | |
| *Lactobacillus casei* | [IF012004] | IFO 12004 |
| *Leuconostoc mesenteroides* subsp. *dextranicum* | [IF03349] | IFO 3349 and |
| *Streptococcus equinus* | [NRIC1139] | NRIC 1139 | and recovering the optically active (R)-2-hydroxy acid derivative of the formula (II) so produced.

22. The process of claim 21, wherein said microorganism has been collected from the culture and resuspended in an aqueous medium prior to treating the said 2-oxo acid.

23. The process of claim 21, wherein said microorganism has been collected from the culture and the cells ground, treated with acetone, or lyophilized prior to treating the said 2-oxo acid.

24. A process for the production of an optically active 2-hydroxy acid derivative represented by the formula (II):

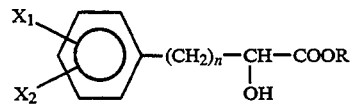

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

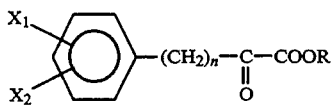

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism is selected from the group consisting of:

| | | |
|---|---|---|
| Lactobacillus plantarum | [IF03070] | IFO 3070 |
| Ashbya gossypii | [IF01355] | IFO 1355 |
| [Endomyces decipiens | IF00102] | |
| Serratia marcescens | [IF03046] | IFO 3046 |
| Esherichia coli | [IF03544] | IFO 3544 |
| Pseudomonas aureofaciens | [IF03522] | IFO 3522 |
| Leuconostoc mesenteroides | [AHU1067] | AHU 1067 |
| Streptococcus faecalis | [IF012964] | IFO 12964 |
| Sporolactobacillus inulinus | [NRIC1133] | NRIC 1133 |
| [Candida pseudotropicalis | IAM4829] | |
| Candida rugosa | [IF00750] | IFO 0750 |
| Pichia burtonii | [IF01986] | IFO 1986 |
| Trigonopsis variabilis | [IF00755] | IFO 0755 |
| [Bacillus subtilis | IF03007] | |
| [Brevibacterium ammoniagenes | IAM1641] | |
| Flavobacterium suaveolens | [IF03752] | IFO 3752 and |
| Paracoccus denitrificans | [IF012442] | IFO 12442 | and recovering the optically active (S)-2-hydroxy acid derivative of the formula (II) so produced.

25. The process of claim 24, wherein said microorganism has been collected from the culture and resuspended in an aqueous medium prior to treating the said 2-oxo acid.

26. The process of claim 24, wherein said microorganism has been collected from the culture and the cells ground, treated with acetone, or lyophilized prior to treating the said 2-oxo acid.

27. A process for the production of an optically active 2-hydroxy acid derivative represented by the formula (II):

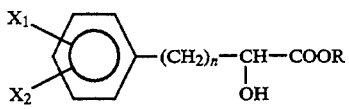

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

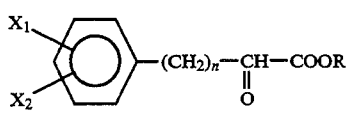

wherein $X_1$, $X_2$, R and n are as previously defined, with a microorganism capable of asymmetrically reducing said 2-oxo acid derivative of the formula (I) into an optically active (R)-form of said 2-hydroxy acid derivative of the formula (II), wherein said microorganism has all of the identifying characteristics of a microorganism selected from the group consisting of:

| | |
|---|---|
| Lactobacillus casei subsp. casei | IFO 12004; |
| Leuconostoc mesenteroides subsp. dextranicum | IFO 3349; |
| Streptococcus equinus | NRIC 1139; |
| Sporidiobolus pararoseus | AHU 3447; and |
| Rhodosporidium toruloides | IFO 0559; | and recovering the optically active (R)-2-hydroxy acid derivative of the formula (II) so produced.

28. A process for the production of an optically active 2-hydroxy acid derivative represented by the formula (II):

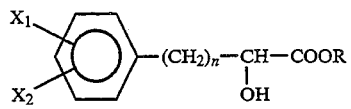

wherein $X_1$ and $X_2$ represent each a hydrogen atom, a halogen atom, a hydroxyl group, a nitro group or an alkyl group, R represents an alkyl or a phenyl group, and n is an integer ranging from 0 to 3, which comprises treating a 2-oxo acid derivative represented by the formula (I):

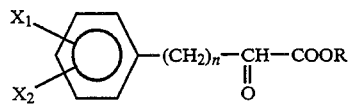

wherein $X_1$, $X_2$, R and n are as previously defined, with a microorganism capable of asymmetrically reducing said 2-oxo acid derivative of the formula (I) into an optically active (S)-form of said 2-hydroxy acid derivative of the formula (II), wherein said microorganism has all of the identifying characteristics of a microorganism selected from the group consisting of:

| | |
|---|---|
| Trigonopsis variabilis | IFO 0755 |
| Lactobacillus plantarum | IFO 3070; |
| Streptococcus faecalis | IFO 12964; |
| Sporolactobacillus inulinus | NRIC 1133; |
| Candida rugosa | IFO 0750; |
| Pichia burtonii | IFO 1986; |
| Ashbya gossypii | IFO 1355; |
| Eserichia coli | IFO 3544; |
| Serratia marcescens | IFO 3046; |
| Pseudomonas aureofaciens | IFO 3522; |
| Leuconostoc mesenteroides | AHU 1067 |
| Flavobacterium suaveolens | IFO 3572; and |
| Paracoccus denitrificans | IFO 12442; | and recovering the optically active (S)-2-hydroxy acid derivative of the formula (II) so produced.

* * * * *